United States Patent [19]

Meseke et al.

[11] Patent Number: 5,007,535
[45] Date of Patent: Apr. 16, 1991

[54] SYRINGE TRAY

[75] Inventors: Curt T. Meseke, Leer/Ostfriesl.; Winfried Winkler, Aachen; Renate Hilbig, Hamm, all of Fed. Rep. of Germany

[73] Assignee: Hammerlit GmbH, Leer/Ostfriesland, Fed. Rep. of Germany

[21] Appl. No.: 412,813

[22] Filed: Sep. 26, 1989

[30] Foreign Application Priority Data

Sep. 26, 1988 [DE] Fed. Rep. of Germany .. 8812156[U]
Jul. 13, 1989 [DE] Fed. Rep. of Germany ........ 3923119
Aug. 23, 1989 [DE] Fed. Rep. of Germany .. 8910067[U]

[51] Int. Cl.$^5$ ............................................. B65D 83/10
[52] U.S. Cl. .................................... 206/366; 206/363; 206/364; 206/562
[58] Field of Search ............... 206/364, 365, 366, 370, 206/379, 443, 477, 483, 486, 562, 563, 565, 459

[56] References Cited

U.S. PATENT DOCUMENTS

| | | | |
|---|---|---|---|
| 2,557,420 | 6/1951 | Elliott | 206/366 |
| 2,962,154 | 11/1960 | Falk | 206/379 |
| 2,966,986 | 1/1961 | Jones | 206/365 |
| 3,107,785 | 10/1963 | Roehr | 206/365 |
| 3,225,914 | 12/1965 | Klein et al. | 206/459 |
| 3,987,895 | 10/1976 | Jamshidi | 206/564 |
| 4,253,830 | 3/1981 | Kazen et al. | 206/379 |
| 4,420,085 | 12/1983 | Wilson et al. | 206/564 |
| 4,445,611 | 5/1984 | Shofu | 206/379 |
| 4,466,539 | 8/1984 | Frauenhoffer | 206/370 |
| 4,485,918 | 12/1984 | Mayer . | |
| 4,503,972 | 3/1985 | Nelligan | 206/379 |
| 4,595,102 | 6/1986 | Cianci et al. | 206/370 |
| 4,596,562 | 6/1986 | Vernon . | |
| 4,770,297 | 9/1988 | Chang | 206/379 |
| 4,802,579 | 2/1989 | Hall et al. | 206/366 |
| 4,836,373 | 6/1989 | Goldman | 206/366 |
| 4,844,249 | 7/1989 | Coulombe | 206/366 |
| 4,850,484 | 7/1989 | Denman | 206/366 |
| 4,863,451 | 9/1989 | Marder | 206/366 |

FOREIGN PATENT DOCUMENTS 0192453 8/1986 European Pat. Off. .
8801602 5/1988 Fed. Rep. of Germany .
8815519 3/1989 Fed. Rep. of Germany .

Primary Examiner—David T. Fidei
Attorney, Agent, or Firm—Robert W. Becker & Associates

[57] ABSTRACT

A syringe tray, for depositing and transporting medical syringes having a hypodermic needle and a cap therefor, including a tray base. In one embodiment a raised portion in the form of a ridge extends upwardly from the plane of the tray base and includes a wall that is provided with holes in which the caps can be disposed in a predetermined manner. Cylinders for receiving the caps can also be provided on the tray base. Alternatively, the tray base itself can be provided with holes for receiving the caps.

18 Claims, 4 Drawing Sheets

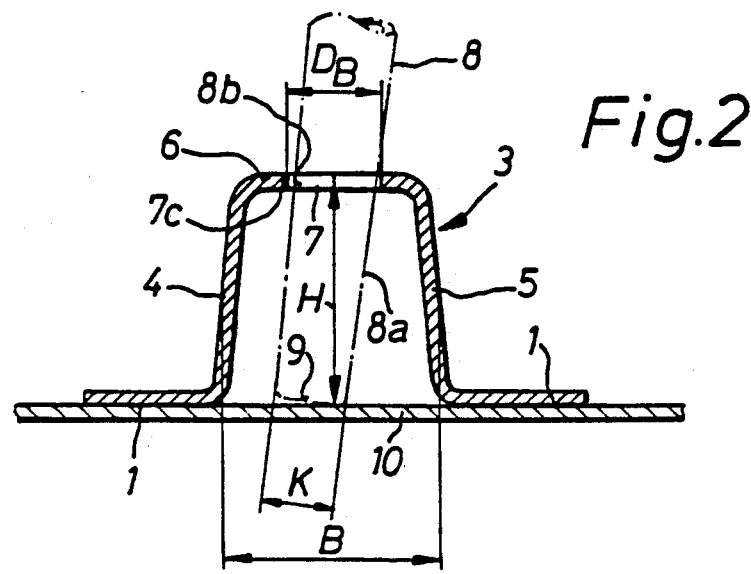
Fig.2
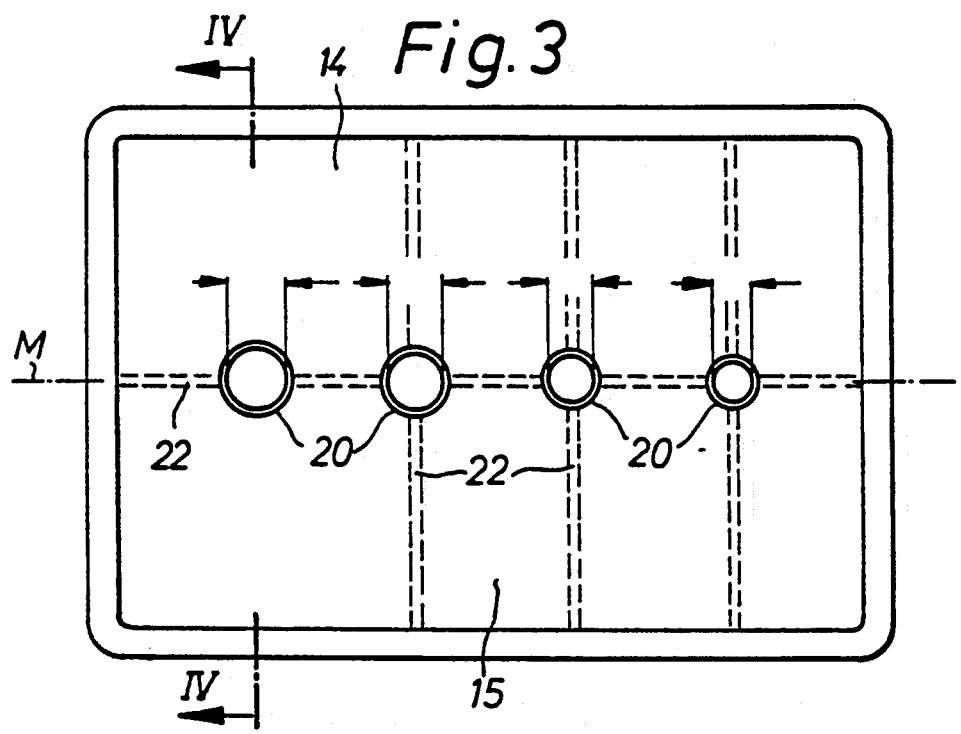
Fig.3
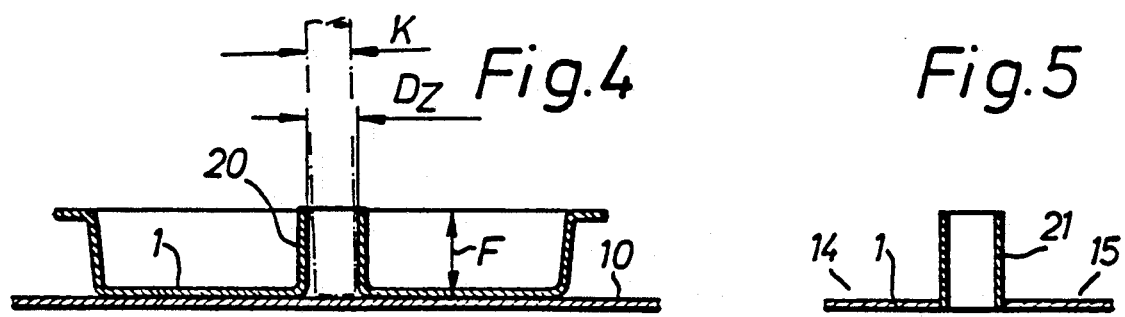
Fig.4
Fig.5

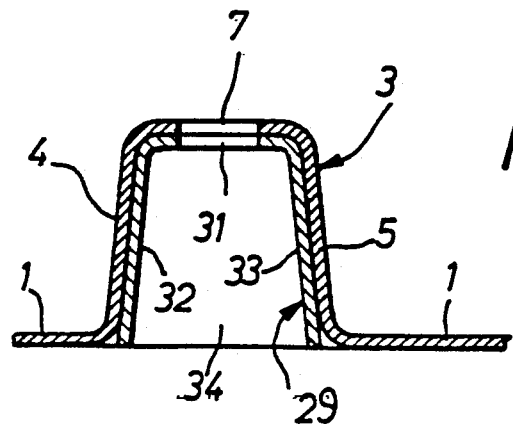
Fig. 8
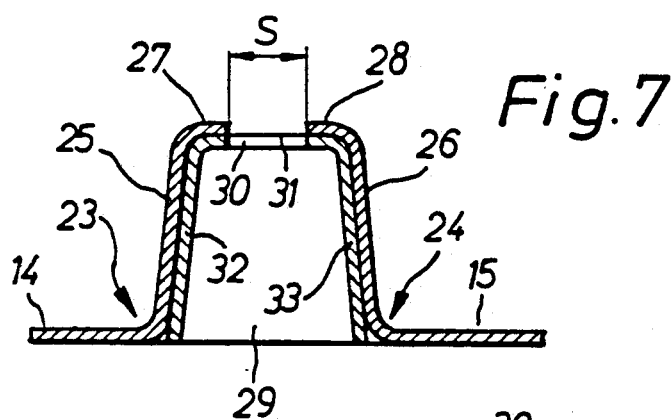
Fig. 7
Fig. 9
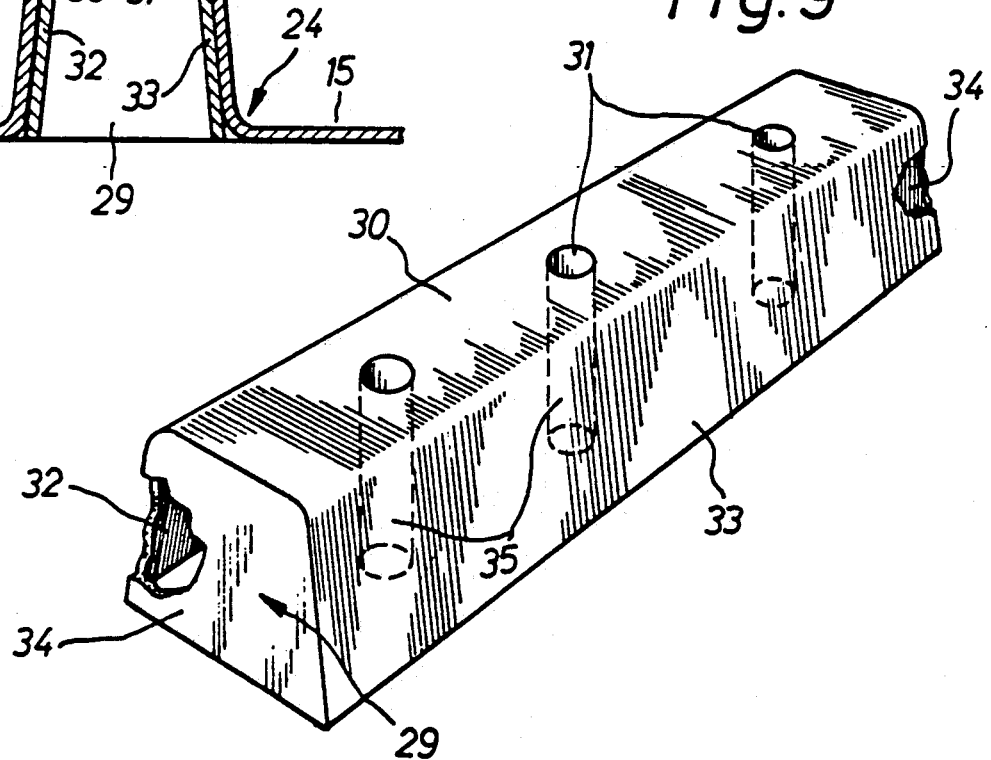
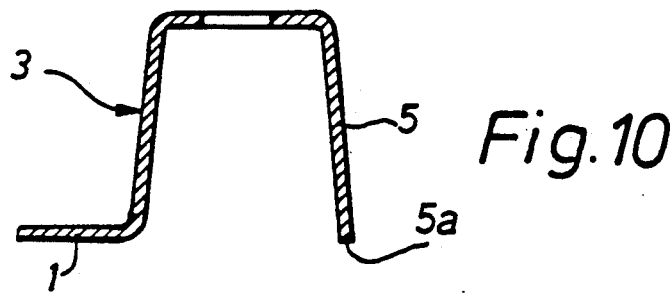
Fig. 10 the present invention. SYRINGE TRAY

SYRINGE TRAY

BACKGROUND OF THE INVENTION

The present invention relates to a syringe tray, for depositing and transporting medical syringes having a hollow or hypodermic needle and a cap therefor, and including a tray base.

DE-GM 88 15 519 discloses a device for facilitating the preparation of medical injections and is in the form of a tray, the tray surface of which has formed therein receiving sections for syringes, ampoules, hypodermic needles, ampoule saws, etc. A container for used hypodermic needles can be exchangeably connected to this container. DE-GM 88 01 602 discloses a tray for medical inserts with a possibly subdivided base and longitudinal and transverse edge members, with the tray forming a generally rectangular enclosure that extends all the way around. The tray surface is subdivided by partitions that are in the form of raised portions and in which are provided recessed portions for the deposition of syringes.

Such trays, as well as the subject matter of the present invention, serve for the transport of medical accessories as well as injection and blood-removal syringes. For an injection or to take blood, the cap that is held on the hypodermic needle is removed, thereby releasing the needle for puncture. After an injection has been given or blood has been taken, the exposed hypodermic needle, which is contaminated after puncture, represents a risk of infection for the doctor, especially with regard to hepatitis or AIDS infection if the introduction of the hypodermic needle into the cap is effected in such a way that the syringe is guided with one hand while the cap is held with the other hand.

U.S. Pat. No. 4,596,562 discloses a hand tool that is supposed to reduce this risk and that is provided with holes having different diameters into which the hypodermic needle caps can be inserted. In this connection, during introduction of the hypodermic needle into the cap, the tool must be held with one hand while the syringe is held with the other hand and the hypodermic needle thereof is introduced into the cap. The advantage over tightly holding the hypodermic needle cap is that the tool is held at a distance from the hypodermic needle by one hand; nonetheless, this holding hand of the user is still in the vicinity of the hypodermic needle. Aside from this, both hands of the doctor are always needed to introduce the hypodermic needle into the cap provided therefor. Holes are provided in this tool in such a way that the hypodermic needle caps are tightly held in the tool, so that to release the cap, which is placed on the hypodermic needle, it is necessary to press the cap out of the hole by stressing the base of the hypodermic needle. EP-OS 0 192 453 and U.S. Pat. No. 4,485,918 show a similar tool. Here the hypodermic needle cap is held in a wedged manner by a hole or a sleeve-like portion of the cup or funnel tool, whereby the side flanges of the tool are intended to protect the thumbs and index finger of the holding hand of the user. If the tool, along with the introduced cap, is placed upon a support surface, for example a table top, the cap must be held tightly in the tool, which is effected by the wedging in the hole or in the sleeve-like portion of the tool, in order to enable an introduction of the used needle into the cap.

The thing to watch with these last-mentioned tools is the basic concept of wedging the hypodermic needle cap in the tool. In so doing, care must be taken that upon release of the cap from the hand tool, the connection between the head of the hypodermic needle and the corresponding end of the cap, which are held tightly together, is not loosened, since otherwise the objective of the cap as a protection against the needle is lost. Therefore, with the described known tools, the cap must be pressed out.

It is an object of the present invention to provide a syringe tray where all contact and hence injury of the user from contaminated hypodermic needles is precluded, where insertion of the hypodermic needle into the cap can be effected without having to use a second hand, and where furthermore the removal of the hypodermic needle cap from the tray does not require a grasping or other action upon the base of the hypodermic needle cap. This means that the tray can be left on its support surface for providing a wedging connection between the hypodermic needle cap and the needle. This should be possible with a straightforward configuration of the tray.

SUMMARY OF THE INVENTION

To realize this object, two embodiments of the invention are provided. The first embodiment proceeds from a ridge in which are provided the receiving holes for the hypodermic needle caps. The second embodiment provides cylindrical raised portions into which the hypodermic needle cap can be inserted.

The advantage of the inventive syringe tray is that it is merely necessary to loosen the hypodermic needle cap from the needle and to introduce the cap in a vertical position into the hole or cylinder. The hypodermic needle cap is in this connection in a vertical or nearly vertical position and is supported on the support surface upon which the tray rests. Since the syringe tray rests on a support surface that is 0.60–1.20 m above the ground, a reliable introduction of the used needle into the cap can be effected from above by the user. Since the cap is disposed in the hole in the cylinder in a nonwedged manner, the cap is not retained in the hole or cylinder when the syringe, along with the used needle and the cap, is removed from the tray from above and is placed in a compartment of the tray.

BRIEF DESCRIPTION OF THE DRAWINGS

The drawings illustrate specific embodiments of the inventive tray; in particular FIGS. 1 and 2 are respectively a perspective view of one exemplary embodiment of the inventive tray and a cross-sectional view taken along the line II—II in FIG. 1, FIGS. 3 and 4 are respectively a further exemplary embodiment of the inventive syringe tray with several cylindrical raised portions disposed in a row, and a cross-sectional view taken along the line III—III in FIG. 3, FIG. 5 is a modification of the embodiment of FIG. 4, FIGS. 7, 8 and 9 show an insert that is held in a ridge of the embodiment of FIGS. 1 and 2, FIG. 10 shows the configuration of the tray edge of a further exemplary embodiment of the inventive tray, FIGS. 11 and 12 respectively show a further exemplary embodiment in a perspective view and in a cross-sectional view taken along the line XII—XII in FIG. 11.

DESCRIPTION OF PREFERRED EMBODIMENTS

Figure 1:
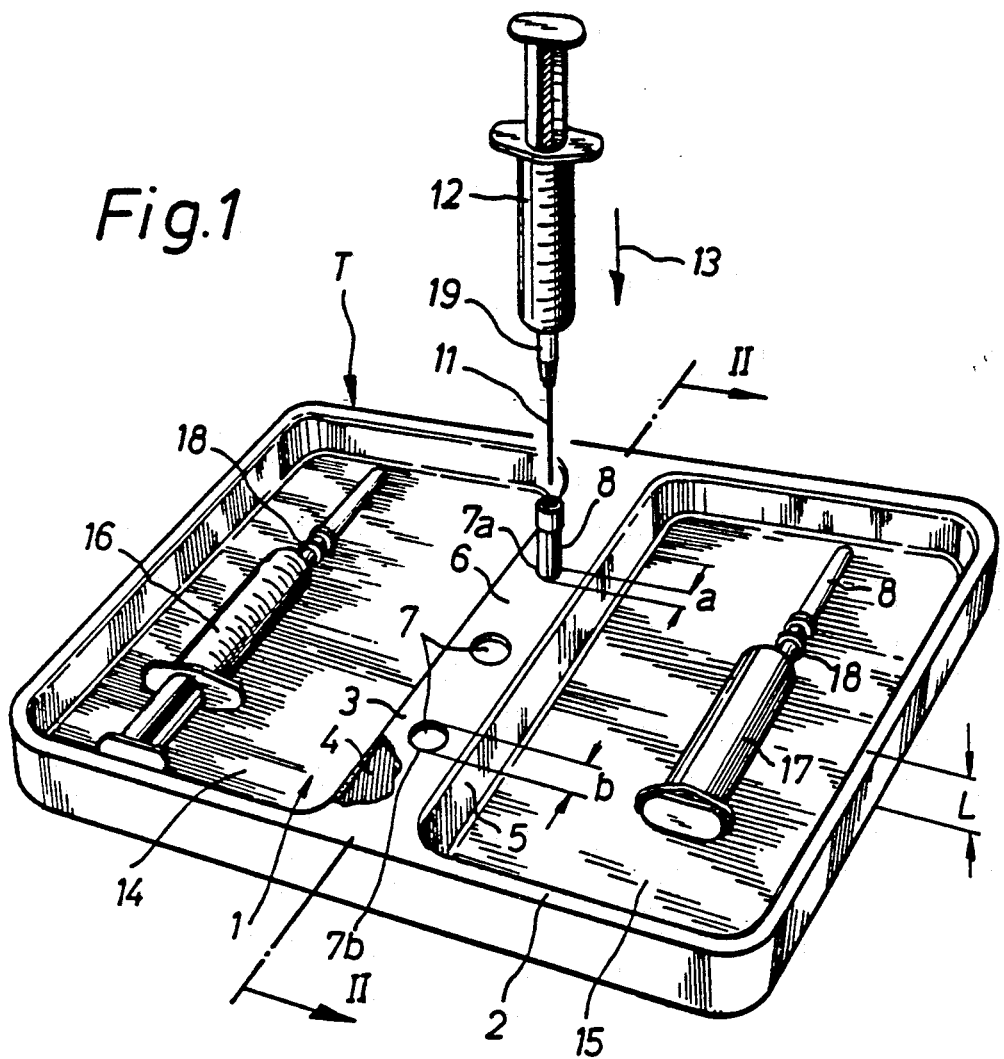

The tray T of the present invention is provided with a base 1 that sits on a non-illustrated surface and that is delimited by a peripheral, collar-like rim 2 that is bent up away from the base. In the embodiment of FIG. 1, a ridge 3 is raised from the plane of the base 1 in the longitudinal or transverse center of the tray; the ridge has two side walls 4, 5 and a top 6. The height H (FIG. 2) of the ridge 3 can correspond to the height L of the rim 2, whereby the ridge preferably has an average width B that is greater than the width of the rim 2.

The tray T is made of injection molded or extruded plastic having properties that are appropriate for its particular application. The top 6 of the ridge 3, which preferably has a trapezoidal or rectangular cross-sectional configuration, is different diameters, in particular in conformity with the diameter of conventional hypodermic needle caps. For example, the hole 7a can have a diameter "a" and the hole 7b can have a larger diameter "b". The diameter $D_B$ of the holes 7 is the same as or less than the height H of the ridge 3, so that the hypodermic needle cap 8 that is placed in the hole 7 is disposed vertically or nearly vertically when its bottom 9 rests upon the support surface 10 of the tray T, for example a table or the shelf of an instrument cart.

The relationship between the opening $D_B$ and the diameter K of the hypodermic needle cap 8 should be such that the cap to the extent possible has no inclination less than 60° when the base portion 8a thereof is inserted through the hole 7. The cap 8 should preferably assume a vertical position, as shown in FIG. 1, so that the used hypodermic needle 11 of the syringe 12 can be introduced in a vertical direction (see arrow 13 in FIG. 1) from above into the syringe cap 8. This assures a maximum probability that the needle 11 will accurately hit the cap 8.

The various diameters of the holes 7 assure that the hypodermic needle cap 8 will be disposed vertically in the holes 7. Even if the user makes a mistake in his selection of the diameter of the holes 7, one is still assured that the hypodermic needle cap will be disposed substantially vertically in the hole 7.

The hypodermic needle cap 8 is held in the hole 7 in such a way that there is still play between the edge 8b of the hypodermic needle cap and the inner rim 7c of the hole 7. This means that the hypodermic needle cap 8 rests freely in the hole 7 and is not wedged therein.

The ridge 3 divides the tray into two compartments 14, 15 such that the unused syringes 16 with the hypodermic needles and caps can be accommodated in the compartment 14, while the used syringes 17 with the corresponding hypodermic needles and caps can be placed in the compartment 15.

The user of a syringe removes from the compartment 14 the unused syringe and removes the hypodermic needle cap 8, which is placed into the appropriate hole 7 of the ridge 8 in the position shown in FIG. 2. After dispensing the injection or drawing blood, the hypodermic needle 11 is then introduced, as shown in FIG. 1, into the vertical cap 8, with the head 18 of the cap becoming tightly connected to the appropriately conically configured head 19 of the hypodermic needle 11. Subsequently, the syringe 12, with the used needle 11 and the wedged-on cap 8, can be removed from the hole 7 in the ridge 3 in a direction opposite to that of the arrow 13. Thereupon, the syringe with the contaminated needle 11 and the cap 8 can be placed in the compartment 15.

In the embodiment illustrated in FIG. 3, in place of the ridge 3 of the embodiment of FIGS. 1 and 2, a row of cylinders 20 is again provided in the longitudinal or transverse center M of the tray T. This tray again has a rim 2 that extends all the way around, with the length F of the cylinders being the same as or greater than the diameter $D_Z$ of the cylinders 20 and also greater than the average diameter K of the cap 8 that rests in the cylinders 20 with freedom of movement of the base 8a of the cap 8.

Here also the cylinders 20 can have a length F that corresponds to the height L of the rim 2.

FIG. 5 illustrates a different possible configuration of the cylinder 20 of FIGS. 3 and 4.

With this embodiment also, the rows of cylinders 20 form a partition that divides the tray into the compartments 14 and 15 of FIG. 1. Additional fin-like walls 22 can bring about a further subdivision of the tray.

In the embodiment of FIG. 7, the tray T comprises two individual parts 23, 24 having side walls 25, 26. The tops of the side walls merge into narrow horizontal strip-like portions 27, 28 that are spaced from one another by a distance S. With this embodiment, an insert unit 29 (FIG. 9) having a trapezoidal cross-sectional configuration is used; the top 30 of the insert is again provided with a row of spaced apart holes 31, preferably of varying diameters. The side walls 32, 33 of such an insert are glued or otherwise joined to the walls 25, 26 of the two individual tray parts, so that again an integral tray with the compartments 14, 15 results. In this manner, trays can be assembled from several individual parts, such as the parts 23, 24, in order to obtain variously sized trays as an assembly of parts. In so doing, the portions 27, 28 of the individual tray parts are embodied as peripheral, collar-like rims that can correspond to the rims 2 of FIGS. 1, 2. To increase the stability of the tray, the insert can be provided with end walls 34 or can be solid.

In order to obtain a tray that is transversely or longitudinally rigid, the block-like insert 29 of FIG. 9 could also be utilized with the embodiment of the tray of FIGS. 1 and 2. In this connection, the side walls 32, 33 of the block-like insert 29 are fused or glued to the side walls 4, 5 of the ridge (FIG. 8).

The insert 29 of FIG. 9 can also be provided with tubular portions 35 that correspond to the cylinders 20 of FIGS. 3–5.

Finally, FIG. 10 illustrates that the ridge 3 can also be embodied as a rim of a tray T, whereby the lower edge 5a of the side wall 5 of the ridge 3 ends at the level of the base 1 of the tray.

Figure 6:
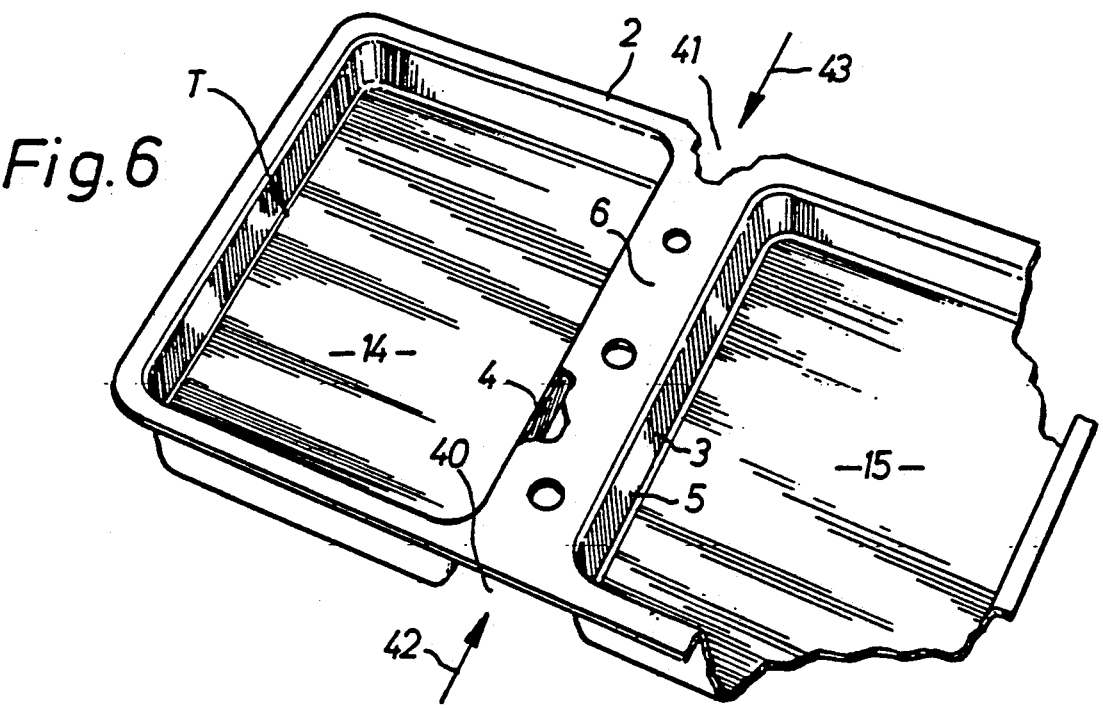
FIG. 6 is a further exemplary embodiment of a syringe tray having a central ridge in which are disposed holes having different diameters.

The arrangement of the ridge 3 and its holes 7, as well as of the cylinders 20, is selected in such a way that no "dead" corners or regions result, so that the tray is easy to clean and disinfect; the ridge 3 as well as the cylinders 20 are open from the bottom for this purpose. The embodiment of FIG. 6 also conforms to this endeavor, with the ends 40, 41 of the ridge being open, whereby the ridge walls 4, 5 and the top 6 are embodied in conformity with the rigidity of the tray. With this embodiment, a cleaning of the inside of the ridge 3 can be undertaken from the direction of the arrows 42, 43.

In order without difficulty and loss of time to be able to reliably recognize that hole 7 that has the diameter that corresponds to the diameter of the cap 8 that is being used, so that this cap can receive as vertical a positioning as possible in the ridge, the ridge can clearly visibly widen from one end to the other in conformity with the increase of the diameter of the holes, which are disposed in a row. The ridge 3 widens in conformity with the increase of the diameter "a" of the holes 7a in FIG. 1 to the diameter "b" of the next plus one hole. The length of the cylinders 20 can also increase in conformity with the increasing diameter of FIG. 3. The height of the ridge could also increase in comparison with the increasing hole diameter.

The ridge 3 as well as the row of cylinders 20 can also have a different orientation to that which is illustrated; for example, the ridge for the row of cylinders can extend at an angle and over a corner of the tray.

As indicated previously, the dimensions of the ridge height, the hole diameter, and the length and diameter of the cylinders 20 is selected in such a way, and are coordinated with one another in such a way, that the cap 8 is disposed vertically or substantially vertically, so that there is no wedging of the cap in the hole or the cylinders with such a force that during a mutual withdrawal of the syringe and cap from the hole or cylinder would release the wedging connection between the needle head 18 and the syringe 8 and would unintentionally remove the needle from the cap. In any case, when the syringe head with the needle is raised or removed, the cap must be taken along without the cap experiencing a longitudinal shearing from the underside of the tray.

Figure 11:
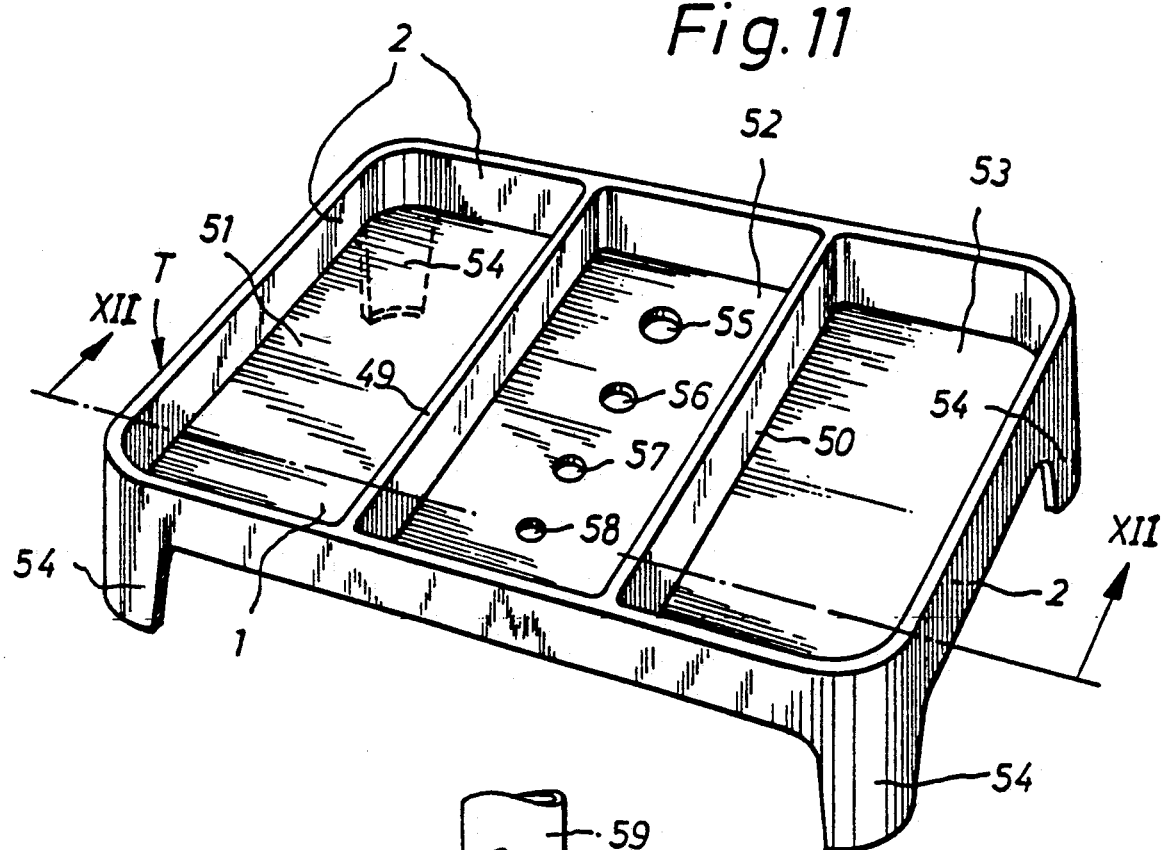
Figure 12:
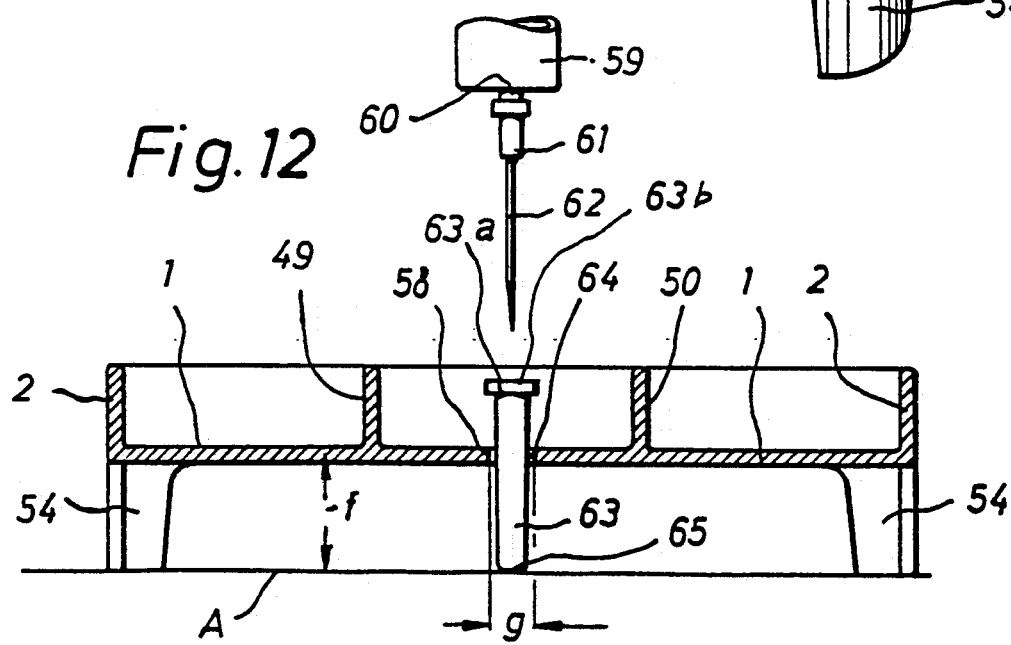
Figure 13:
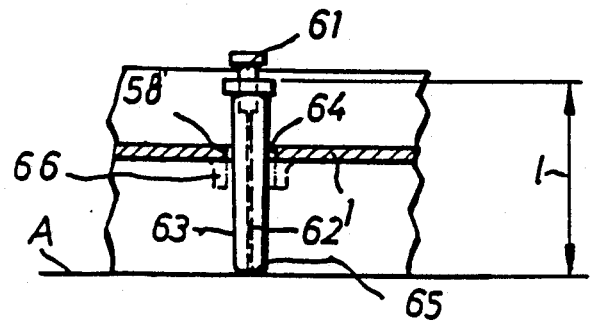
FIG. 13 shows the location and positioning of the parts of the embodiment of FIG. 11.

In the embodiment of FIGS. 11 to 13, the tray T is again provided with a tray base 1 that is planar and extends parallel to a tray support surface A. The tray base 1 is surrounded by a peripheral, collar-like rim 2 that extends all the way around; furthermore disposed in the central portion of the tray are partitions 49, 50 via which, together with the rim 2, compartments 51, 52, 53 are formed, with at least the compartments 51 and 53 serving for the accommodation of medical syringes. The size of the tray, as well as the size of the compartments 51 and 53, is selected for this purpose. At its four corners, the tray is provided with feet 54 via which the base 1 is spaced by a distance F from the tray support surface A. This distance has a particular magnitude, which will be explained subsequently.

The central compartment 52 of the tray is provided with a row of holes 55, 56, 57, 58 that have different diameters, with the diameter continuously decreasing from the largest hole 55 to the smallest hole 58. The holes, or the region around them, can be provided with colored markings to facilitate recognition of the diameter of the holes.

In this situation also the medical syringes are provided with a syringe body 59 having a hollow conical extension 60. The hollow, similarly conical head 61 of the hypodermic needle can be placed on this extension, where it is tightly held. The hypodermic needle 62 is associated with a cap 63, which here also has the purpose of accommodating the hypodermic needle 62, with the upper portion 63a of the cap being tightly held upon the conical head 61 of the needle 62. In conformity with the magnitude of the injection syringe, the hypodermic needle caps 63 have different diameters, which are taken into account by the different diameters of the holes 55-58.

The holes 55-58 have a diameter "g" that relative to the hypodermic needle caps of different magnitudes always leaves a small space 64 that enables a freedom of movement of the caps 63 in the holes 55-58, whereby, as illustrated in FIGS. 12 and 13, the hypodermic needle caps 63 assume a vertical or substantially vertical position, whereby the base 65 rests upon the support surface A. This positioning of the hypodermic needle caps 63 in the holes 55-58 in a predetermined manner is important to the extent that during insertion of the hypodermic needle 62 into the cap 63 a wedging connection occurs between the head 61 of the needle 62 and the end 63a of the cap 63, and on the other hand during an upward movement of the syringe body 59 the cap 63 can be freely removed from the holes 55-58 without the cap 63 becoming stuck in the holes 55-58 and the aid of the second hand of the user of the tray being necessary in order to push the cap out of the hole from the underside of the tray. As a result, any danger of the second hand of the user becoming punctured by the contaminated hypodermic needle 62 is precluded. In other words, here also the wedging force between the head 61 and the upper conical portion 63a of the cap 63 must be guaranteed to be greater than the friction between the cap and the wall of the hole. Therefore, essentially wedge-free in this sense signifies the described connection of the cap with the head of the needle on the one hand and the withdrawal of the cap, which is connected with the head 61, from the hole.

The height F of the base 1 above the support surface A is selected in such a way that the cap 63 assumes a vertical or substantially vertical and essentially wedge-free position, as described above. In this connection, the distance F should preferably be no less than 1/5 of the length "l" of the longest cap.

In order to enhance the vertical or substantially vertical position of the hypodermic needle cap 63, the edges of the holes 55-58 can be flanged downwardly or upwardly in a collar-like manner relative to the support surface A, as indicated by the collar 66 in FIG. 13.

As evident from the above, the base 65 of the cap 63 rests upon the tray support surface A, and is thereby held in the holes 55-58 in a predetermined manner. However, the cap 63 can also be suspended in the holes; the distance F between the support surface A and the base 1 is then greater than the distance between the support surface A and the annular widened portion or bead 63b (FIG. 12). In this situation, the cap 63 is then suspended by its widened portion or bead on the rim of the hole in such a way that it rests in an essentially wedge-free manner in the holes 55-58.

The present invention is, of course, in no way restricted to the specific disclosure of the specification and drawings, but also encompasses any modifications within the scope of the appended claims.

We claim:

1. A syringe tray for depositing and transporting medical syringes having a hypodermic needle and a cap therefor, including a tray base and further comprising:
   means associated with said tray base and including hole means, with said caps being adapted to be disposed in said hole means in a predetermined manner, said means associated with said tray base comprising at least one raised portion that is in the form of a ridge that extends upwardly from the plane of said tray base and includes a wall that is remoted from said tray base and is provided with said hole means, said ridge having two ends and increasing in width from one end to the other, said hole means being successively disposed holes that increase in diameter from said one end of said ridge to the other, with said increase in width of said ridge corresponding to said increase in diameter of said holes.

2. A syringe tray for depositing and transporting medical syringes having a hypodermic needle and a cap therefor, including a tray base and further comprising: means associated with said tray base and including hole means, with said caps being adapted to be disposed in said hole means in a predetermined manner, said means associated with said tray base comprising several cylinders that project from said tray base and form said hole means, with said cylinders being disposed in a row and dividing said tray base into compartments.

3. A syringe tray according to claim 1, in which said hole means has a diameter that is greater than a cap diameter so as to allow movement of said cap in said hole means.

4. A syringe tray according to claim 1, in which said hole means has an edge portion that is bent upwardly or downwardly, in the axial direction of said hole means, to form a collar.

5. A syringe tray according to claim 1, which includes several hole means having differently colored adjoining regions to improve recognition of the diameters thereof.

6. A syringe tray according to claim 1, in which said ridge divides said tray base into compartments.

7. A syringe tray according to claim 1, which has a collar-like rim, with the height of said ridge corresponding to the height of said rim.

8. A syringe tray according to claim 1, in which the height of said ridge increases in conformity with the increase in diameter of said holes.

9. A syringe tray according to claim 8, in which the height of said ridge is at least as great as the diameter of said caps disposed therein.

10. A syringe tray according to claim 2, in which each cylinder has an open bottom end.

11. A syringe tray according to claim 2, in which each cylinder is a tubular element having a base that is fused to said tray base.

12. A syringe tray according to claim 2, which has a collar-like rim, with the height of each cylinder-corresponding to the height of said rim.

13. A syringe tray according to claim 2, in which said cylinders increase in diameter from one end of said row to the other, with the height of said cylinders increasing in conformity with the increase in diameter of said cylinders.

14. A syringe tray according to claim 2, in which the length of said cylinder is at least as great as the diameter of said caps disposed therein.

15. A syringe tray according to claim 1, in which said means associated with said tray base is part of said tray base and forms said hole means, with said tray base being disposed at a distance from a support surface for said tray, with said distance being equal to from 1/5 of the length of a cap to greater than said length.

16. A syringe tray according to claim 15, in which said hole means comprises several holes having different diameters.

17. A syringe tray according to claim 16, in which said cap has a head with an annular bead-like portion, with said distance between said support surface and said tray base being greater than the distance of said bead-like portion from said support surface, with said cap being suspended in an essentially wedge-free manner in said holes.

18. A syringe tray according to claim 1, in which said means associated with said tray base comprises at least one raised portion that is in the form of a ridge that extends upwardly from the plane of said tray base and includes a wall that is remote from said tray base and is provided with said hole means, said means associated with said tray base also comprising not only a block-like unit that is inserted into said ridge but also cylinders that are disposed in said unit and have hole means that are aligned with said hole means of said ridge.

* * * * *